| (12) United States Patent  O'Neill | (10) Patent No.: US 9,044,550 B2 |
|---|---|
| | (45) Date of Patent: Jun. 2, 2015 |

(54) NEEDLE COVER WITH SITE PREPARATION TIP

(75) Inventor: Dennis O'Neill, Pompano Beach, FL (US)

(73) Assignee: JMS NORTH AMERICA CORPORATION, Hayward, CA (US)

( * ) Notice: Subject to any disclaimer, the term of this patent is extended or adjusted under 35 U.S.C. 154(b) by 580 days.

(21) Appl. No.: 12/307,099

(22) PCT Filed: Jul. 2, 2007

(86) PCT No.: PCT/US2007/015369
§ 371 (c)(1),
(2), (4) Date: May 11, 2009

(87) PCT Pub. No.: WO2008/005441
PCT Pub. Date: Jan. 10, 2008

(65) Prior Publication Data
US 2009/0270882 A1    Oct. 29, 2009

Related U.S. Application Data

(60) Provisional application No. 60/818,606, filed on Jul. 5, 2006.

(51) Int. Cl.
*A61B 17/50* (2006.01)
*A61M 5/32* (2006.01)
*A61M 1/36* (2006.01)

(52) U.S. Cl.
CPC .......... *A61M 5/3202* (2013.01); *A61M 1/3655* (2013.01)

(58) Field of Classification Search
CPC ................ A61B 17/50; A61B 17/54; A61B 2017/00761; A61B 2017/00774; A61B 2017/320008; A61M 5/3202; A61M 5/3204; A61M 5/3213

USPC ........ 132/73, 73.5, 75.3, 76.2, 76.5; 604/192, 604/197, 198, 263, 272, 533–539; 206/571; 606/52, 131, 159–161, 185, 167, 210, 606/211
See application file for complete search history.

(56) References Cited

U.S. PATENT DOCUMENTS 622,386 A * 4/1899 Peery ............................. 606/160
2,081,540 A * 5/1937 Hosselet ....................... 606/211
(Continued)

FOREIGN PATENT DOCUMENTS

| AU | 2007269631 A1 | 1/2008 |
| DE | 29719826 U1 | 12/1998 |

(Continued)

OTHER PUBLICATIONS www.thefreedictionary.com/trough retrieved on Oct. 26, 2011, definition of the word "trough" indicated by annotated arrow.*

(Continued)

*Primary Examiner* — David Eastwood
(74) *Attorney, Agent, or Firm* — Rutan & Tucker, LLP

(57) ABSTRACT

A needle cover is disclosed which includes a site preparation tip at a distal end of a needle cover body. The tip may be configured with rounded and/or beveled edges in order to facilitate material removal from a cannulation site. The proximal end of the needle cover body may include features to facilitate handling, removal of the needle, and operation of the needle cover in removing material, such as a scab, from a cannulation site.

19 Claims, 3 Drawing Sheets

(56) References Cited

U.S. PATENT DOCUMENTS

| | | | | |
|---|---|---|---|---|
| 2,297,714 | A | * | 10/1942 | Nesbitt ............ 132/149 |
| 3,054,182 | A | * | 9/1962 | Whitton, Jr. ............ 606/138 |
| 4,641,662 | A | * | 2/1987 | Jaicks ............ 600/570 |
| 4,915,698 | A | * | 4/1990 | Levenson ............ 604/192 |
| 5,013,305 | A | * | 5/1991 | Opie et al. ............ 604/192 |
| 5,169,391 | A | * | 12/1992 | Vogel ............ 604/177 |
| 5,554,126 | A | * | 9/1996 | Filley ............ 604/192 |
| 5,620,455 | A | * | 4/1997 | Grigoletto ............ 606/167 |
| 5,752,936 | A | | 5/1998 | Chen |
| 6,726,649 | B2 | | 4/2004 | Swenson et al. |
| 7,055,527 | B2 | * | 6/2006 | Tien ............ 132/75.6 |
| 8,235,951 | B2 | * | 8/2012 | Hund et al. ............ 604/192 |
| 8,506,536 | B2 | * | 8/2013 | Schnell ............ 604/263 |
| 2002/0095122 | A1 | * | 7/2002 | Shaffer ............ 604/263 |
| 2003/0125675 | A1 | * | 7/2003 | Caizza et al. ............ 604/263 |
| 2004/0153038 | A1 | | 8/2004 | Guala |
| 2004/0193211 | A1 | * | 9/2004 | Voegele et al. ............ 606/205 |
| 2005/0038391 | A1 | * | 2/2005 | Wittland et al. ............ 604/192 |
| 2005/0070854 | A1 | | 3/2005 | Wright |
| 2005/0199099 | A1 | | 9/2005 | Schaeffer |

FOREIGN PATENT DOCUMENTS

| | | |
|---|---|---|
| JP | 63130052 U | 8/1988 |
| JP | 8224306 A | 9/1996 |
| JP | 3073155 U | 11/2000 |
| WO | 9000075 A2 | 1/1990 |
| WO | 2006017835 A3 | 11/2007 |

OTHER PUBLICATIONS www.thefreedictionary.com/frame retrieved on Oct. 26, 2011, definition of the word "frame" indicated by annotated arrow.*

AU 2007269631 filed Jul. 2, 2007 Notice of Acceptance dated Dec. 6, 2012.

CA 2,656,090 First Examiner's Report dated Oct. 3, 2013.

PCT/US2007/015369 filed Jul. 2, 2007 International Preliminary Report on Patentability and Writen Opinion dated Jul. 2, 2008.

PCT/US2007/015369 filed Jul. 2, 2007 International Search Report dated Jul. 2, 2008.

AU 2007269631 filed Jul. 2, 2007 Office Action dated Mar. 27, 2012.

EP 07810145.8 filed Jul. 2, 2007 European Search Report dated Dec. 19, 2012.

JP 2009-518338 filed Dec. 26, 2008 Decision to Grant dated Dec. 14, 2012.

JP 2009-518338 filed Dec. 26, 2008 Official Action dated Feb. 7, 2012.

JP 2009-518338 filed Dec. 26, 2008 Official Action dated Sep. 4, 2012.

* cited by examiner

NEEDLE COVER WITH SITE PREPARATION TIP

PRIORITY

This application is a U.S. national stage application under 35 USC §371 of International Application No. PCT/US2007/015369, filed Jul. 2, 2007, which claims the benefit of priority to U.S. Provisional Patent Application No. 60/818,606, filed Jul. 5, 2006, each of which is incorporated by reference into this application as if fully set forth herein.

BACKGROUND

Hemodialysis is a common treatment for kidney failure, especially when a kidney transplant cannot be performed. During hemodialysis, a patient's blood is removed (a small amount at a time) and circulated through a hemodialysis machine to remove impurities and regulate fluid and chemical balances. The purified blood is then returned to the patient. Blood can be removed from the patient through an access point to the patient's bloodstream. This access point is usually in the patient's arm, and allows blood to be removed and returned quickly, efficiently, and safely during hemodialysis or other procedures requiring frequent access to the patient's bloodstream.

The area within which an access point may be established may be formed by constructing an arteriovenous fistula (AV fistula), which is the surgical connection of an artery to a vein. AV fistulas are commonly used to form areas for access points because once formed, they can be used for years, and are less likely than other methods to produce clots or become infected. When an AV fistula is created, the connection between the artery and the vein increases blood flow through the vein, causing the vein to enlarge and strengthen. This change allows a greater amount of blood to pass through the vein, thereby increasing the efficiency of the hemodialysis, and also facilitates repeated insertions into the vein. The insertion of two needles (one to withdraw blood from the patient and one to return blood to the patient) into the area formed by the AV fistula are typically required for every hemodialysis treatment session. In some cases, a "ladder" methodology is used in which the access point for needle insertion in the AV fistula is gradually and systematically moved up the entire length of the AV fistula to prevent any one area from being weakened by excessive needle sticks in a short period of time.

An alternative approach is the constant site cannulation method in which the same needle insertion site is used for repeated hemodialysis treatment sessions. When a new needle insertion site is first selected, a sharp needle is used at an aseptic site to puncture the skin and vessel. Over time (e.g. after about six cannulations of the same site with a sharp needle), a mature needle insertion site will form with a "tunnel" or "track" of scar tissue. To properly form the mature site, the same needle insertion angle and depth of penetration is generally employed, usually by the same clinician. After a mature needle insertion site has been formed, subsequent site cannulations may be performed using a blunt needle. Prior to performing constant site cannulation with a blunt needle, the cannulation site must be prepared. First, aseptic techniques are utilized to cleanse the cannulation site (e.g. by washing the site with soap and water or an antimicrobial agent, preferably using circular movements). Next, the scab from the previous cannulation must be removed. (It should be understood that after the previous hemodialysis treatment session is completed and the needles are removed, a scab, or crust, will form at the entrance of the site).

Current practice for removing the scabs from constant sites differs widely from country to country and region to region. In the U.S., the scabs on sites are removed with sterile hypodermic needles, sterile or non-sterile devices (such as tweezers), or are scrubbed off with a water and soap solution. However, each of these practices creates potential problems. For example, the use of hypodermic needles carries a risk of damage to tissues surrounding the scab. Also, the use of needles or other devices requires additional sterilization procedures as well as the expense of the devices themselves. Non-sterile devices carry the risk of infection. In addition, the method of scrubbing off residual scabs does not work with all patients and may cause irritation of surrounding tissue. After the scab has been removed and the site is once again disinfected, the blunt needle is removed from its sterile packaging and its cover removed. The blunt needle is then advanced along the established scar tissue tunnel track using a consistent angle and depth of insertion. This technique has been shown to generally reduce the cutting of tissue surrounding the established scar tissue tunnel or track. Other potential advantages of the constant-site cannulation technique using blunt needles include reduced pain, hematoma, infections, thrombosis, infiltrations, and missed needle sticks.

Although the constant-site cannulation technique is believed to be advantageous for reasons such as those mentioned above, Applicant has recognized that removal of the scab in a sterile manner without requiring additional sterilization procedures, while reducing the risk of damage or irritation to tissues surrounding the scab, can be accomplished through the use of a needle cover with a site preparation tip.

BRIEF SUMMARY

Accordingly, an aseptic needle cover is described herein, the needle cover including a site preparation tip at a distal end of the needle cover for removing scabs or other material prior to cannulation without posing a sharp object injury threat. The needle cover includes a body that is generally hollow or tubular and may be essentially cylindrically shaped. The site preparation tip may be formed as a scoop integrally formed at the distal end of the needle cover body and shaped as a partial cutaway beveled portion of an extended hollow cylindrical portion of the needle cover body, forming a trough and a rounded tip for lifting a scab as it separates from the patient's skin. Other site preparation tips may be employed, including but not limited, to a slightly fork-like embodiment to retain the scab and lift the scab from either side as the scab removal tip is advanced along the scab, a tip with substantially straight edges to reduce the chance that the tip will slip to one side of the scab as the scab removal tip is advanced along the scab, a curved tip to press down on the skin adjacent to the scab and ensure that the removal tip reaches under material such as a scab prior to removal of the scab, or a tip configured with opposing members that flex toward one another (e.g., like a tweezer) to help grasp and remove the scab.

The proximal (open) end of the needle cover body may include a circumferential ring or flange integrally formed with the needle cover body and/or a plurality of raised sections integrally formed with the needle cover body to provide stops and gripping surfaces on the outside of the needle cover. The circumferential ring may also serve the purpose of providing a larger opening for receiving the needle holder (hub), luer or luer lock of a needle assembly. Air vent grooves may also be formed in the inner surfaces of the circumferential ring and the needle cover body to enable air to escape from or enter into the interior of the needle cover body and provide for easier insertion or removal of the needle assembly from the needle cover body. The circumferential ring also exposes a step surface on the interior of the needle cover body that acts as a stop to prevent the needle and its corresponding hub, luer or luer lock from extending too far into the interior of the needle cover body.

Any of the site preparation tips may include an anti-slip finger restraint which may be formed as one or more raised circumferential sections located towards the proximal end of the needle cover body to reduce the chance of finger slippage and contamination of the cannulation site and/or site preparation tip at the distal end as the needle cover body is grasped. The tweezer-like embodiment may further or alternatively include a finger guard on each opposing member to prevent finger slippage and contamination of the cannulation site and/or the opposing members at the distal end as they are grasped.

In one embodiment, a needle cover includes a hollow needle cover body including an open proximal end for receiving a needle and a closed distal end, and a tip including a beveled edge extending from the closed distal end. In another embodiment, a needle set includes a needle assembly, and a needle cover removably coupled to the needle assembly, the needle cover including a hollow needle cover body having a closed distal end and an open proximal end, and a site preparation tip including a rounded distal edge extending from the closed distal end of the needle cover body.

In one embodiment, a method for removing material from a cannulation site, includes removing material from a cannulation site prior to cannulation utilizing a site preparation tip provided on a needle cover. A coupled needle assembly and needle cover are removed from a sterile pack after a cannulation site has been cleansed and immediately prior to use. The needle cover body is grasped and manipulated onto the scab/crust covering the cannulation site, the tip of the needle cover being utilized to scrape and remove the scab/crust. In some situations, scab removal may be effectuated by gently depressing the skin adjacent to the scab with the tip of the needle cover and then advancing the tip of the needle cover toward the scab until it is lifted and separated from the surrounding skin. The cannulation site is once again cleansed following removal of the scab/crust. The needle assembly is then separated from the needle cover and the needle is inserted into the cannulation/access site.

These and other embodiments, methods, features and advantages will become more apparent to those skilled in the art when taken with reference to the following more detailed description of the invention in conjunction with the accompanying drawings that are first briefly described.

DESCRIPTION OF THE PREFERRED EMBODIMENTS

The following description should be read with reference to the drawings. The drawings, which are not necessarily to scale, depict selected embodiments and are not intended to limit the scope of the invention. The description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Embodiments of the present invention relate generally to an aseptic needle cover shaped for removing scabs or other material at the needle insertion site prior to insertion of the needle, without posing a sharp object injury threat. It should be noted that the needle cover, as described herein, may be used for a number of different applications, such as, but not limited to, covering blunt needles and removing scabs/crust prior to constant site cannulation for hemodialysis treatment sessions, and for covering other types of needles and removing scabs or other types of material prior to insertion of the needles for other types of treatments. The needle cover and corresponding needle assembly (needle and hub) together comprise a needle set.

Figure 1A:
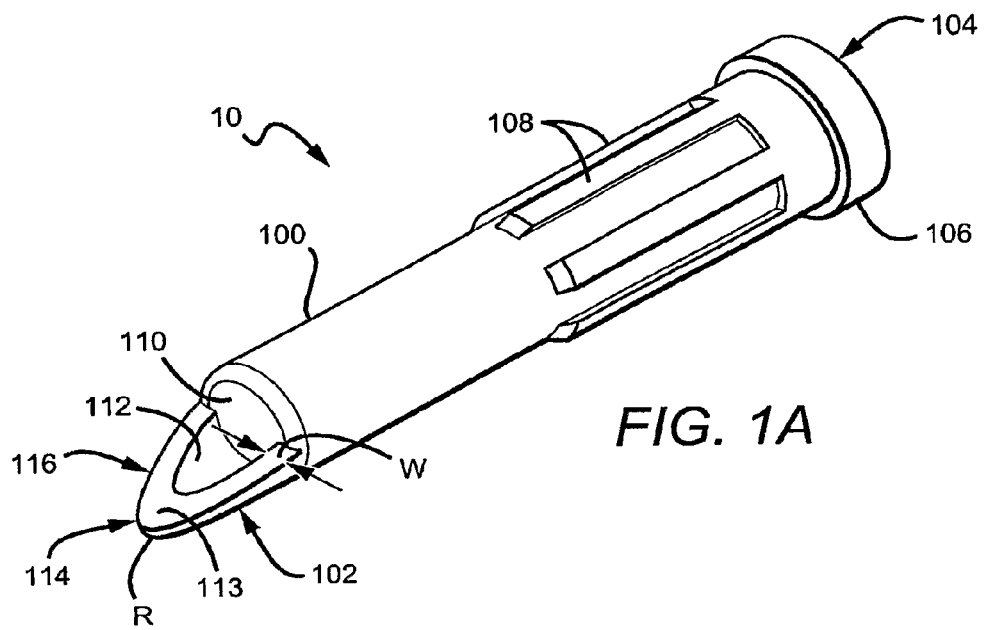
FIG. 1A is a perspective view of one embodiment of a needle cover with a scoop design.

FIG. 1A shows one embodiment of a needle cover with a site preparation tip. Needle cover 10 includes a scoop-shaped material removal tip 102 for removing scabs or other material prior to cannulation, and a body 100 that is generally hollow or tubular and may be essentially cylindrically shaped as shown in FIG. 1A, but which may also be gradually tapering or have square, rectangular, triangular, oval or other cross-sectional shapes. The needle cover body 100 may be formed from a material such as, but not limited to, polyurethane, polyethylene, polypropylene, and the like. A needle assembly (not shown) is insertable into, or removable from, an open proximal end 104 of the hollow needle cover body 100 along a longitudinal axis of the needle cover. The proximal end 104 of the needle cover body 100 may include a circumferential ring or flange 106 integrally formed with the needle cover with a larger radius than the needle cover. The flange 106 may provide a retaining surface to assist a person or machine in inserting the needle cover body 100 over a needle assembly, and may also provide a larger opening in the needle cover to receive the needle. The needle cover body 100 may also include a plurality of raised sections 108 integrally formed with the needle cover body and oriented parallel to the longitudinal axis of the needle cover body 100. In an alternative embodiment, the raised sections may also be formed as a plurality of circumferential rings around the needle cover body 100. The raised sections 108 may be located at the proximal end 104 of the needle cover body 100 to provide a gripping surface located away from the tip 102, so that a sterile environment for the tip 102 is maintained.

Figure 1B:
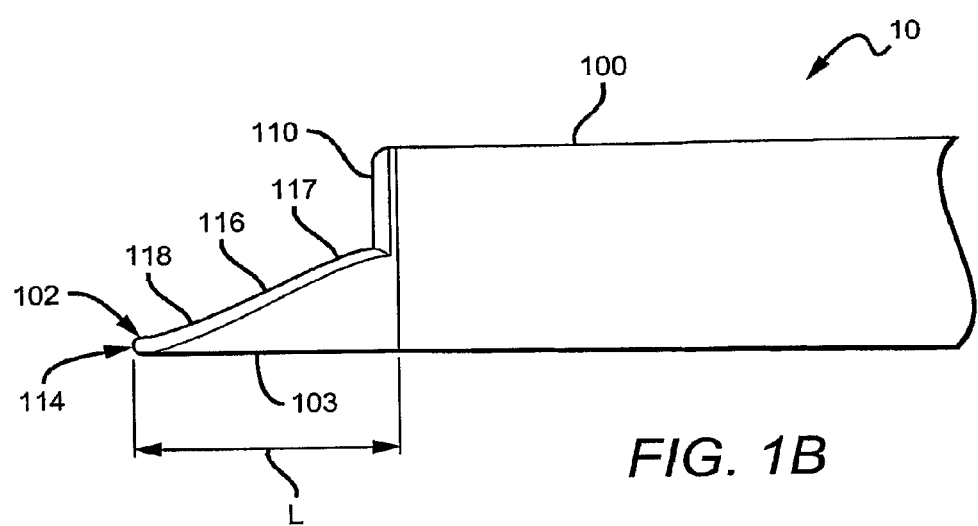
FIG. 1B is a side view of the distal end of the needle cover of FIG. 1A.

The tip 102 may be integrally formed at a distal end of the needle cover body 100, or separately formed and affixed to the distal end of the needle cover body. The tip 102 may be shaped as a partial cutaway beveled portion of an extended hollow cylindrical portion of the needle cover body 100, forming a trough or valley 112, although in alternative embodiments the tip 102 may be shaped as a partial cutaway portion of an extended solid cylindrical portion of the needle cover body 100, in which case no trough or valley 112 would exist (e.g., the tip would include a planar upper surface). The tip 102 extends from the closed end 110 of the needle cover body 100 a length L and forms a rounded distal edge 114, including a radius R, and includes a distal surface 113 and beveled surfaces 116, including a width W, to facilitate the lifting of material from a patient's skin. The beveled surfaces 116, having approximately equivalent widths W in the embodiment of FIGS. 1A-1B, extend from the closed end 110 of the body 100 to the distal surface 113, the beveled surfaces 116 and distal surface 113 together framing the trough or valley 112. As shown in profile in FIG. 1B, the beveled edges of the tip 102, including the edges of the beveled surfaces 116 and the edges of the distal surface 113, are generally non-planar, including a convex portion 117 followed by a concave portion 118. In other embodiments, the beveled edges of the tip 100 are generally planar (e.g., FIG. 2B), while in still other embodiments, the tip 102 includes beveled edges without a distal surface 113 and/or without surfaces 116. A base surface 103 of the tip 102 is substantially the same as a corresponding surface of the distal end of the body (i.e., semi-circular in cross-section) from which it extends. In one embodiment, the tip 102 extends from the distal end of the needle cover body 100 a length L in the range of approximately 4 mm to approximately 8 mm, preferably approximately 6 mm, has a radius R of the rounded distal tip in the range of approximately 1.0 mm to approximately 2.0 mm, preferably approximately 1.5 mm, and has a width W of the beveled surfaces in the range of approximately 0.5 mm to approximately 1.5 mm, preferably approximately 1 mm.

Figure 1C:
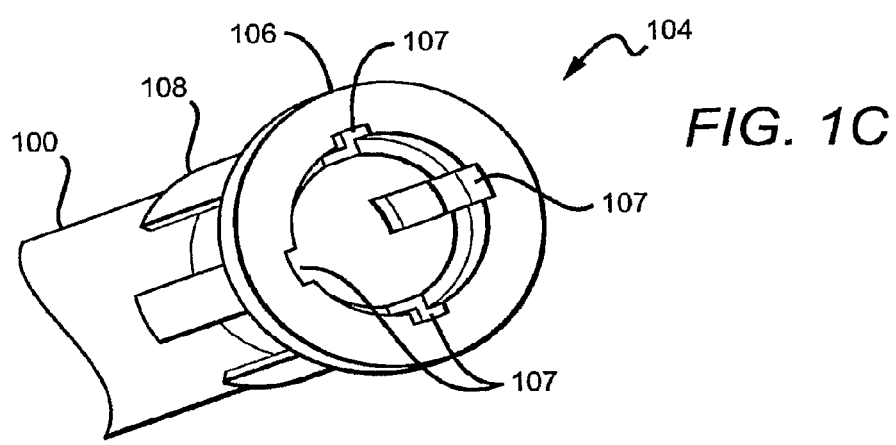
FIG. 1C is a perspective view of the proximal end of the needle cover of FIG. 1A.
Figure 1D:
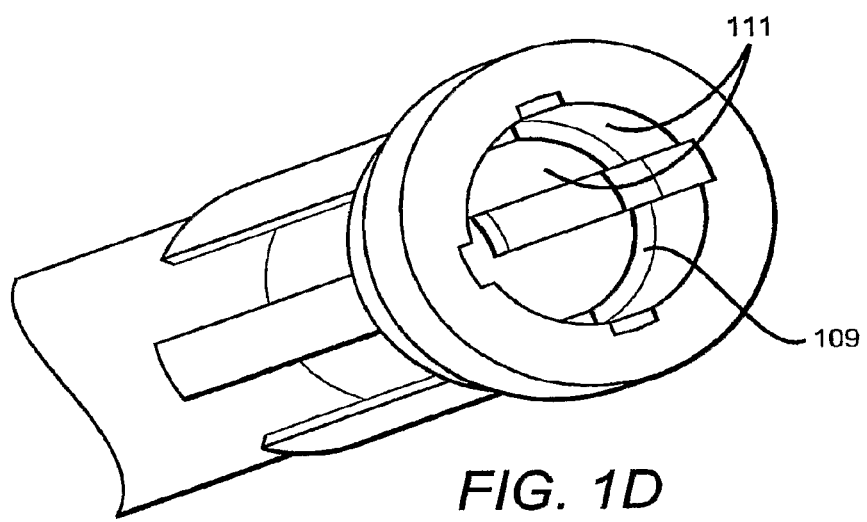
FIG. 1D is a perspective close-up view of the proximal end of the needle cover of FIG. 1A.

FIG. 1C is a perspective view of the open proximal end 104 of the exemplary needle cover body 100 for receiving a needle or other instrument. The cylindrical circumferential ring 106 integrally formed at the proximal end 104 of the needle cover body 100 provides a larger opening for receiving or removing a needle. Air vent grooves 107 may be formed in the inner surfaces of the circumferential ring 106 and the needle cover body 100 to enable air to escape from or enter into the interior of the needle cover body and provide for easier insertion or removal of the needle from the needle cover 10. FIG. 1D is a perspective close-up view of the open proximal end 104 of the exemplary needle cover body 100, illustrating the feature of a step surface 109 that acts as a stop to prevent a needle and its corresponding hub, luer or luer lock from extending too far into the interior of the needle cover body. The step surface 109 is generally a planar surface perpendicular to the longitudinal axis of the needle cover body 100. Inner surfaces 111 of the circumferential ring 106 and the needle cover body 100 may be designed and shaped to receive and secure a hub, luer or luer lock or other portion of the needle assembly.

Figure 2A:
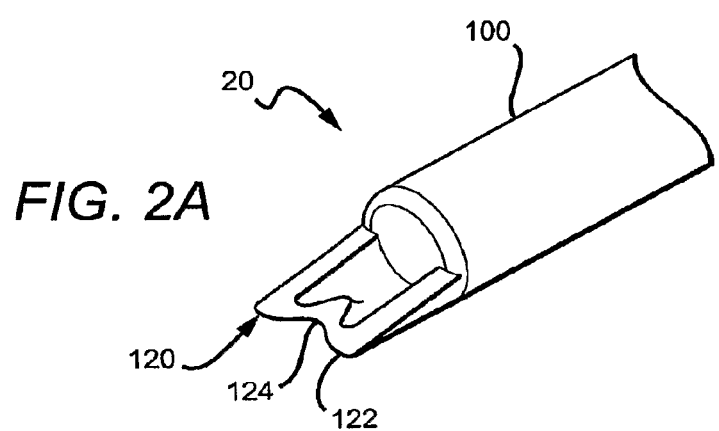
FIG. 2A is a perspective close-up view of the distal end of another embodiment of a needle cover.
Figure 2B:
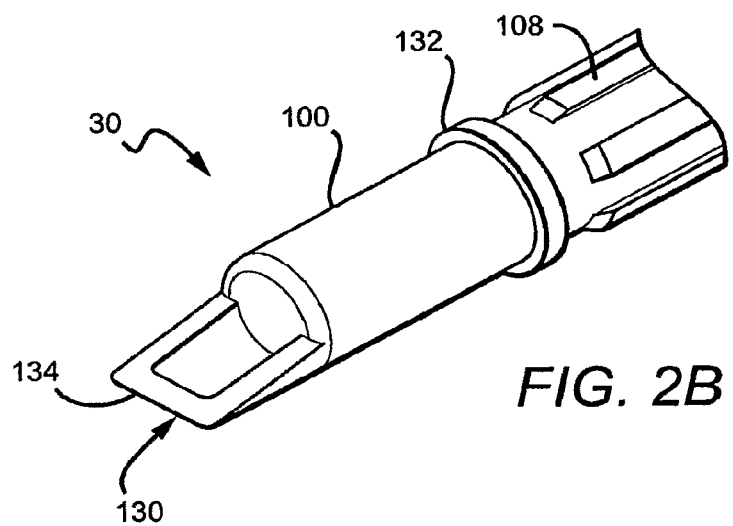
FIG. 2B is a perspective close-up view of the distal end of another embodiment of a needle cover.

FIG. 2A is a perspective close-up view of the distal end of a needle cover 20 with a needle cover body 100 and a site preparation tip 120. The tip 120 has a fork-like shape, which in this embodiment has dual extended portions 122 that have a curved shape, which are separated by a recessed portion 124. In other embodiments the extended portions 122 may be less curved (i.e., more pointed) and/or may number more than two (i.e., three or more extended portions). The extended portions 122 act to retain a scab or other material and lift the scab from either side as the scab removal tip is advanced along the scab. FIG. 2B is a perspective close-up view of a needle cover 30 with a site preparation tip 130 and an anti-slip finger restraint 132. The scab removal tip 130 of FIG. 2B is beveled with a flat front edge 134 to reduce the chance that the tip 130 will slip to one side of the scab as the site preparation tip 130 is advanced along the scab. The sides of the tip 130 are also substantially straight so that the tip 130 includes a perimeter with substantially straight edges. The anti-slip finger restraint 132, shown in FIG. 2B as a continuous raised circumferential section reduces the chance of finger slippage and contamination of the site preparation tip 130 as the needle cover body 100 is grasped at the plurality of raised sections 108. Although the restraint 132 is shown as a circumferential section in FIG. 2B, in other embodiments, the restraint 132 may be any raised section on the needle cover body 100 that provides a barrier to prevent one or more fingers from sliding distally along an outer surface of the needle cover body 100.

Figure 2C:
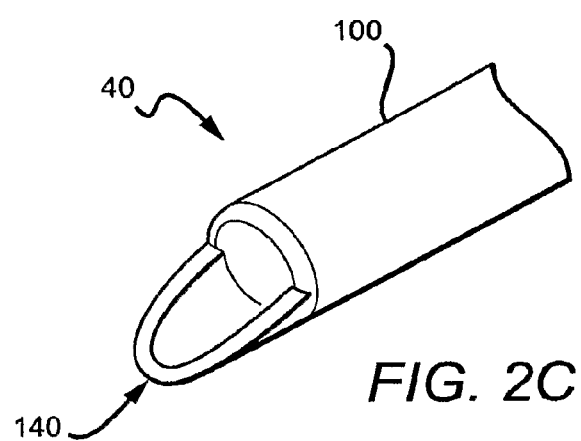
FIG. 2C is a perspective close-up view of the distal end of another embodiment of a needle cover.
Figure 2D:
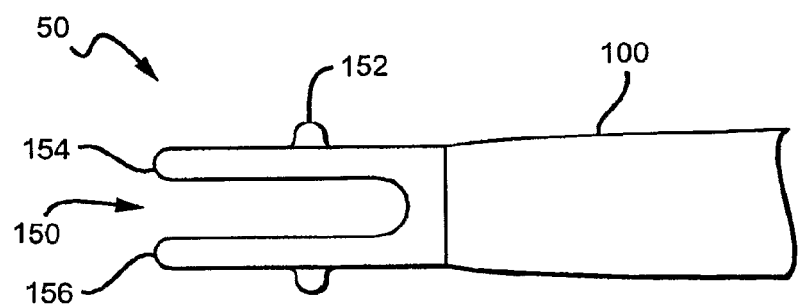
FIG. 2D is a perspective close-up view of the distal end of another embodiment of a needle cover.

FIG. 2C is a perspective close-up view of a needle cover 40 with site preparation tip 140. The site preparation tip 140 is formed in a curved shape with a distal end slightly less pointed (i.e, with a larger radius) than tip 102 of FIG. 1A. FIG. 2D is a side close-up view of a needle cover 50 with site preparation tip 150 and optional finger guard 152. The site preparation tip 150 of FIG. 2D is formed as tweezers to help grasp the scab prior to its removal. Plastic or other material of a thickness to provide suitable flexibility and elasticity may be used to form the opposing members 154, 156 of the tip 150. Pressure exerted behind the finger guards 152 on opposing member 154, 156 in a direction toward a longitudinal axis of the needle cover 50 serves to bring the members 154, 156 together. The finger guards 152 prevent movement of fingers in a distal direction toward the distal end of the members 154, 156 in the event of slippage, thereby avoiding potential contamination of the tip 150. It should be understood that the embodiments of FIGS. 2A-D are exemplary only, and that other site preparation tip designs fall within the scope of the present invention.

As described above, after aseptic techniques are utilized to cleanse the cannulation site, the scab from the previous cannulation must be removed. The needle cover as described herein provides an aseptic method of removing scabs from hemodialysis or other access sites without requiring the use of additional devices and does not pose a sharp injury threat (e.g., as would be present in the standard practice of utilizing a separate needle to remove the scab).

According to a preferred method of use, the needle assembly and needle cover 10 coupled together as a needle set are removed from a sterile pack after a cannulation/access site has been cleansed and immediately prior to use. The needle cover body 100 is grasped with the needle assembly remaining therein, the needle cover tip 102 being positioned first over the cannulation site and then onto the cannulation site covering material (e.g., scab, crust, etc.), the tip 102 being manipulated to scrape or otherwise remove the scab/crust from the cannulation site. In some situations, removal of the cannulation site covering material may be accomplished by gently depressing the skin adjacent to the covering material with the tip 102 of the needle cover and then advancing the tip 102 toward the covering material until it is lifted and separated from the surrounding skin and cannulation site. The cannulation site is once again cleansed following removal of the scab/crust. The needle assembly is then separated from the needle cover 10 by grasping in the other hand (e.g. the left hand if the right hand is holding the needle cover 10) and pulling apart. The needle of the needle assembly is then inserted into the cannulation/access site without delay.

The added scab removal functionality of the needle cover, as described herein, eliminates the need for other instruments such as tweezers or hypodermic needles, eliminates the inconvenience and dangers associated with their use (including needle stick), and eliminates the time and cost of sterilizing such additional instruments, if sterilization is performed. If aseptic methods are not normally performed with separate scab removal instruments, embodiments of the present invention further reduce the risk of infection by eliminating the use of non-sterile instruments. In addition, if these additional scab removal instruments are of the single-use type, embodiments of the present invention eliminate the cost of the instruments themselves.

This invention has been described and specific examples have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A needle set comprising:
    a needle; and
    a needle cover, comprising:
    a body region including an open end and a closed end; and
    a tip designed to remove a scab from a patient including opposing beveled side surfaces with a width and an end surface extending from the opposing beveled side surfaces in an axial direction away from the body region, wherein the opposing beveled side surfaces each include a convex portion and a concave portion extending axially along the opposing beveled side surfaces;
    wherein the needle cover is coupled to the needle prior to use of the needle to protect at least a portion of the needle.

2. The needle set according to claim 1, wherein the width is in a range of approximately 0.5 mm and approximately 1.5 mm.

3. The needle set according to claim 1, wherein the end surface of the tip includes a rounded distal edge with a radius.

4. The needle set according to claim 3, wherein the radius is in a range of approximately 1.0 mm and 2.0 mm.

5. The needle set according to claim 1, wherein the tip has a length in a range of approximately 4 mm to approximately 8 mm.

6. The needle set according to claim 1, wherein the tip includes a base surface with substantially the same shape as a corresponding outer surface of the closed end of the body region.

7. The needle set according to claim 1, wherein the body region comprises a plurality of raised sections integrally formed on an outer surface thereof.

8. The needle set according to claim 1, wherein the body region comprises a circumferential finger restraint integrally formed on an outer surface thereof.

9. The needle set according to claim 1, wherein the body region comprises a circumferential ring integrally formed on an outer surface of the open end thereof, the circumferential ring including a larger inner diameter than an adjacent portion of the body region.

10. The needle set according to claim 9, further comprising one or more air vent grooves formed on an inner surface of the open end of the body region.

11. The needle set according to claim 9, further comprising a step surface at the open end of the body region generally perpendicular to a longitudinal axis of the body region.

12. A needle set, comprising:
    a needle; and
    a needle cover removably coupled to the needle, the needle cover comprising:
    a hollow needle cover body including an open proximal end for receiving the needle and a closed distal end;
    a circumferential ring integrally formed at the open proximal end of the needle cover body; and
    a removal tip including opposing beveled side surfaces with a width and an end surface extending from the opposing beveled side surfaces in an axial direction away from the hollow needle cover body, wherein the opposing beveled side surfaces each include a convex portion and a concave portion extending axially along the side surfaces, the removal tip configured to retain a scab and lift the scab as the removal tip is advanced along the scab.

13. The needle set according to claim 12, further comprising a finger guard located on one or more extended portions.

14. The needle set according to claim 12, further comprising one or more air vent grooves formed in an inner surface of the circumferential ring.

15. The needle set according to claim 12, wherein an inner surface of the circumferential ring is shaped to receive and secure a hub, luer, luer lock, or other portion of a needle assembly.

16. The needle set according to claim 1, wherein the opposing beveled side surfaces and the end surface together frame a trough, the trough closed at its base by a base surface of the removal tip.

17. A system, comprising:
    a needle for accessing a blood vessel in a patient; and
    a scab remover having an elongated body portion and a tip, wherein the tip has opposing beveled side surfaces with a width and an end surface extending from the opposing beveled side surfaces in an axial direction away from the elongated body portion, wherein the opposing beveled side surfaces each include a convex portion and a concave portion extending axially along the opposing beveled side surfaces, wherein the tip is shaped to facilitate removing a scab from a patient;
    wherein the scab remover is removably attached to the needle prior to use of the needle.

18. The system according to claim 17, wherein the scab remover is indirectly attached to the needle prior to use of the needle.

19. The system according to claim 17, wherein the scab remover includes an open end and is shaped to retain the needle within the scab remover.

* * * * *